United States Patent
Benner

(10) Patent No.: US 10,912,525 B2
(45) Date of Patent: Feb. 9, 2021

(54) ADJUSTMENT METHOD FOR A MARKING LASER BEAM, CORRESPONDING ADJUSTMENT SYSTEM AND IMAGING MODALITY

(71) Applicant: Siemens Healthcare GmbH, Erlangen (DE)

(72) Inventor: Thomas Benner, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 360 days.

(21) Appl. No.: 15/968,799

(22) Filed: May 2, 2018

(65) Prior Publication Data

US 2018/0317862 A1 Nov. 8, 2018

(30) Foreign Application Priority Data

May 4, 2017 (DE) .................. 10 2017 207 512

(51) Int. Cl.
*A61B 6/04* (2006.01)
*A61B 5/055* (2006.01)
*A61B 6/03* (2006.01)

(52) U.S. Cl.
CPC ......... *A61B 6/0492* (2013.01); *A61B 5/055* (2013.01); *A61B 5/0555* (2013.01); *A61B 6/03* (2013.01); *A61B 6/032* (2013.01)

(58) Field of Classification Search
CPC ......... A61B 5/055; A61B 5/0555; A61B 6/03; A61B 6/032; A61B 6/0492
USPC ........ 356/139.1, 399–401; 600/41, 414, 425, 600/426
See application file for complete search history.

(56) References Cited

U.S. PATENT DOCUMENTS

| 5,142,559 | A | 8/1992 | Wielopolski et al. |
| 6,647,282 | B2 | 11/2003 | Hair |
| 2007/0291267 | A1* | 12/2007 | Rockseisen ............. A61B 6/08 356/399 |
| 2008/0043237 | A1 | 2/2008 | Grimm et al. |
| 2013/0165767 | A1 | 6/2013 | Darrow et al. |

OTHER PUBLICATIONS

German Office Action dated Oct. 20, 2017 for German Application No. 2017P04315DE.

* cited by examiner

*Primary Examiner* — Colin W Kreutzer
(74) *Attorney, Agent, or Firm* — Harness, Dickey & Pierce, P.L.C.

(57) ABSTRACT

An adjustment method is for a marking laser beam of an imaging modality. The marking laser beam includes a central beam and at least one peripheral beam and extends from a laser source to a detection plane. The detection plane includes a central target position for the central beam and at least one peripheral target position for the at least one peripheral beam and a detection unit. The detection unit is embodied to capture whether the marking laser beam is striking at least one of the target positions. In an embodiment, the method includes a first adjustment of the marking laser beam via an adjusting unit, until it strikes the central target position; and a second adjustment of the marking laser beam via the adjusting unit, until it strikes the at least one peripheral target position. The marking laser beam will also be kept at the central target position.

23 Claims, 7 Drawing Sheets

ADJUSTMENT METHOD FOR A MARKING LASER BEAM, CORRESPONDING ADJUSTMENT SYSTEM AND IMAGING MODALITY

PRIORITY STATEMENT

The present application hereby claims priority under 35 U.S.C. § 119 to German patent application number DE 102017207512.0 filed May 4, 2017, the entire contents of which are hereby incorporated herein by reference.

FIELD

At least one embodiment of the invention generally relates to an adjustment method for a marking laser beam of a medical imaging apparatus, in particular to an adjustment method for a marking laser beam comprising a central beam and at least one peripheral beam. At least one embodiment of the invention further generally relates to an adjustment system for a marking laser beam comprising a laser source for creating the marking laser beam, an adjusting unit for adjusting the same, a detection unit for capturing the marking laser beam in at least one target position corresponding to an adjustment target of the marking laser beam and a control unit for carrying out the adjustment method. At least one embodiment of the invention further generally relates to an imaging modality for adjustment of a marking laser beam.

BACKGROUND

To prepare for the examination of a patient via a medical imaging apparatus, for example a magnetic resonance tomograph or a computed tomograph, a laser will usually be used as an orientation aid. A laser beam is emitted via the laser, which illuminates the region of interest of the patient. A laser beam in the shape of cross hairs is used in such cases for example. A patient couch with the patient supported thereon is then driven or moved such that the cross hairs of the laser light illuminate a defined point within the region of interest of the patient, for example a particular landmark of the patient. In this way the position of the patient on the patient couch or relative to the medical imaging apparatus respectively is defined, so that the patient is subsequently moved precisely to the intended examination position within the medical imaging apparatus and the examination can be carried out explicitly at the region of interest of the patient.

An example of such a method is described in US patent application US 2013/0165767 A1.

As a rule the laser is arranged on the outer housing of a medical imaging apparatus, above the entry of the tunnel of a magnetic resonance tomograph for example. The course of the laser beam is accordingly set to a defined distance from the isocenter of the imaging apparatus. If the medical imaging apparatus is serviced, repaired or if other mechanical work is carried out on it, the housing complete with laser must be removed in order to do this. Minimal offset or inclination of the housing during the subsequent re-installation can lead to the laser beam being out of adjustment, for example the course of its beam can be displaced, inclined or rotated in relation to the adjusted course. The danger now exists of an imprecise positioning of the patient in the medical imaging apparatus, a reduced quality of the recorded images associated therewith and—at least with apparatuses based on x-ray technology—an unnecessary radiation load on or even radiation damage to the patient. In order, after servicing or repair work, to make possible an exact positioning of an examination object in the medical imaging apparatus, the laser beam must thus be adjusted once again. This is a complex, time-consuming process, which must be carried out manually by operating personnel on a regular basis, as described for example in U.S. Pat. No. 6,647,282 B2.

SUMMARY

At least one embodiment of the present invention provides alternate ways that make it possible to adjust a marking laser beam quickly, precisely, and without the assistance of operating personnel.

At least one embodiment of the present invention is achieved by an adjustment method, adjustment system and/or imaging modality. Preferred and/or alternate, advantageous embodiment variants are the subject matter of the claims.

Features, advantages and alternate forms of embodiment mentioned here are likewise also to be transferred to the other claimed subject matter and vice versa. In other words physical claims (which are directed to a method for example) can also be further developed with features that are described or claimed in conjunction with one of the devices. The corresponding functional features of the method are embodied in such cases by corresponding physical modules or units.

On the one hand, at least one embodiment of the present invention relates to an adjustment method for a marking laser beam of an imaging modality, wherein the marking laser beam comprises a central beam in its center and at least one peripheral beam in an outer area of the marking laser beam, wherein the marking laser beam extends from a laser source generating the marking laser beam through to a detection plane, wherein the detection plane comprises a central target position for the central beam and at least one peripheral target position for the at least one peripheral beam and a detection unit, wherein the detection unit is embodied to capture whether the marking laser beam is striking at least one of the target positions, wherein the method comprises:

First adjustment of the marking laser beam via an adjusting unit, until it strikes the central target position, and Second adjustment of the marking laser beam via the adjusting unit, until it strikes the at least one peripheral target position, wherein the marking laser beam will also be kept at the central target position.

At least one embodiment of the present invention also relates to an adjustment system for a marking laser beam of an imaging modality, comprising A laser source for generating the marking laser beam, which propagates from the laser source through to a detection plane and comprises a central beam in its center and at least one peripheral beam in its outer area, A detection unit arranged in the detection plane, wherein the detection plane comprises a central target position for the central beam and at least one peripheral target position for the at least one peripheral beam and the detection unit is configured to capture the marking laser beam striking at least one of the target positions, An adjusting unit, which is configured to adjust the marking laser beam, and A control unit, which is configured, together with detection unit and adjusting unit, to carry out an embodiment of the inventive adjustment method.

At least one embodiment of the invention further relates to an imaging modality for auto adjustment of a marking laser beam comprising an inventive adjustment system.

BRIEF DESCRIPTION OF THE DRAWINGS

The characteristics, features and advantages of this invention described above, as well as the manner in which these are obtained, will become clearer and easier to understand in conjunction with the following description of example embodiments, which are explained in greater detail in conjunction with the drawings. This description does not restrict the invention to these example embodiments. In different figures the same components are provided with identical reference characters. The figures are as a rule not true-to-scale. In the figures.

DETAILED DESCRIPTION OF THE EXAMPLE EMBODIMENTS

Figure 1:
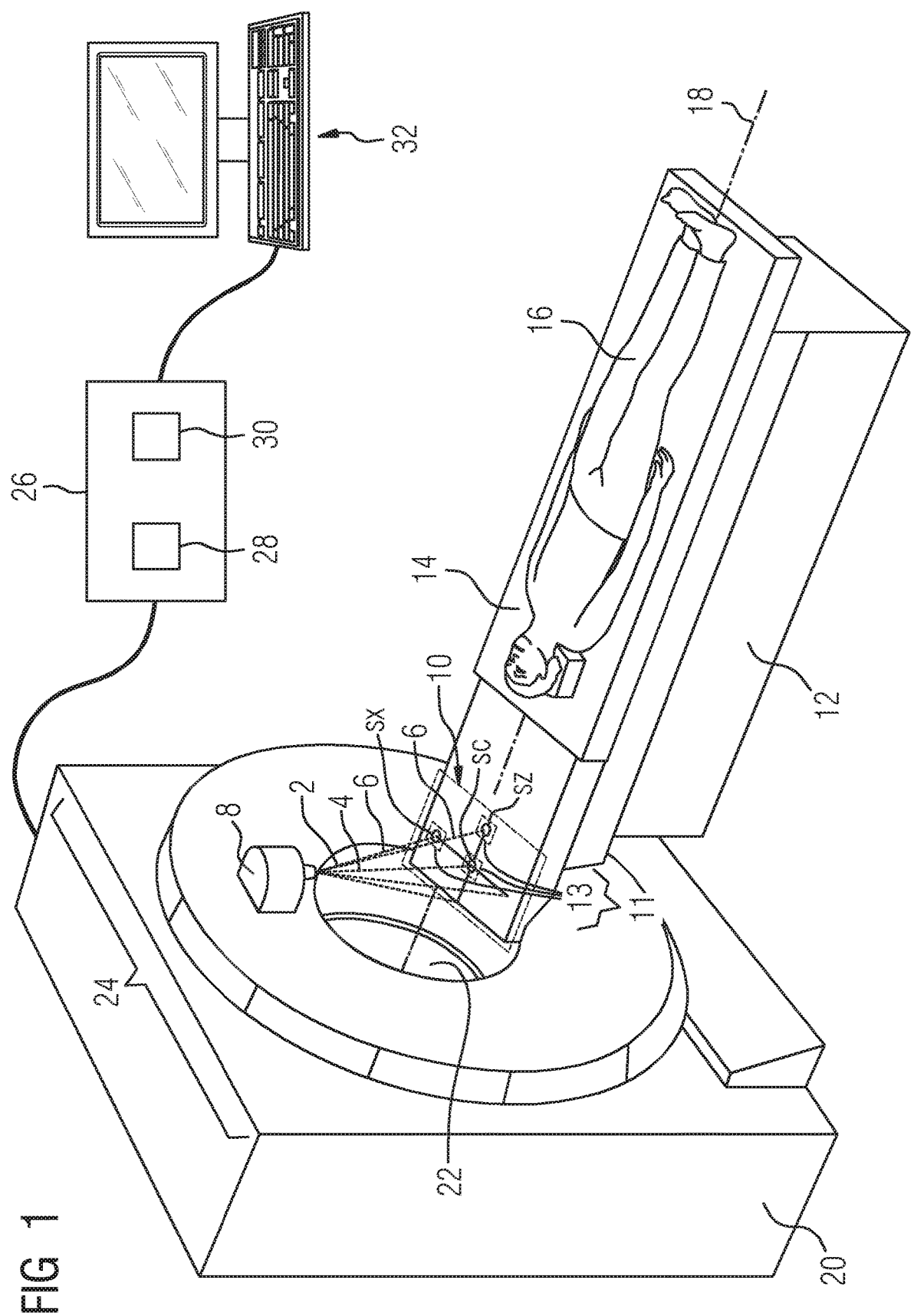
FIG. 1 shows a schematic diagram of an inventive imaging modality in an example embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

On the one hand, at least one embodiment of the present invention relates to an adjustment method for a marking laser beam of an imaging modality, wherein the marking laser beam comprises a central beam in its center and at least one peripheral beam in an outer area of the marking laser beam, wherein the marking laser beam extends from a laser source generating the marking laser beam through to a detection plane, wherein the detection plane comprises a central target position for the central beam and at least one peripheral target position for the at least one peripheral beam and a detection unit, wherein the detection unit is embodied to capture whether the marking laser beam is striking at least one of the target positions, wherein the method comprises:

First adjustment of the marking laser beam via an adjusting unit, until it strikes the central target position, and Second adjustment of the marking laser beam via the adjusting unit, until it strikes the at least one peripheral target position, wherein the marking laser beam will also be kept at the central target position.

At least one embodiment of the present invention also relates to an adjustment system for a marking laser beam of an imaging modality, comprising A laser source for generating the marking laser beam, which propagates from the laser source through to a detection plane and comprises a central beam in its center and at least one peripheral beam in its outer area, A detection unit arranged in the detection plane, wherein the detection plane comprises a central target position for the central beam and at least one peripheral target position for the at least one peripheral beam and the detection unit is configured to capture the marking laser beam striking at least one of the target positions, An adjusting unit, which is configured to adjust the marking laser beam, and A control unit, which is configured, together with detection unit and adjusting unit, to carry out an embodiment of the inventive adjustment method.

At least one embodiment of the inventive adjustment method aims to adjust, to move or to steer or deflect a marking laser beam of an imaging modality into a position that corresponds to a target position of the adjustment method or an adjustment target for the marking laser beam. The target position of the adjustment method corresponds to a position of the marking laser beam with a fixed predetermined or previously defined and known location or fixed predetermined and previously defined distance to an imaging modality, in particular to its isocenter. In other words the target position of the adjustment method describes the initial or start position of the marking laser beam for an alignment of an examination object in relation to the imaging modality before an image measurement.

The target position of the adjustment method of at least one embodiment includes a first central target position and at least one further peripheral target position. The central target position determines the position in a detection plane that the central beam of the marking laser beam is to assume and the at least one peripheral target position determines the position in the detection plane that a peripheral beam of the marking laser beam is to assume at the end of the adjustment method.

Accordingly, in at least one embodiment, the marking laser beam comprises a central beam, which runs in the center of the beam pattern, its geometrical center or its geometrical center of gravity and at least one peripheral beam, which runs in the periphery or in an outer area of the beam pattern, in particular at an outer edge of the beam pattern. Preferably the marking laser beam comprises a plurality of peripheral beams, from which the marking laser beam pattern is produced.

For example, the beam pattern as cross hairs can be embodied with cross arms arranged fixed in relation to one another, not necessarily arranged at right angles. In this case the central beam can run in the crossing point of the laser lines forming the cross arms and the at least one peripheral beam at the outer edge of a cross arm. As an alternative the beam pattern can be embodied as a circle or oval, with central point marking in each case, or as a triangular, square, rectangular, trapezoidal or diamond shaped or polygonal frame, with central point marking in each case, wherein the frame lines can be embodied closed or at least partly open, then in the form of laser line segments. Alternate beam patterns are likewise conceivable, provided they are formed by a central beam and at least one peripheral beam. As well as central beam and peripheral beams, the inventive marking laser beam can comprise further beams that contribute to the beam pattern, without departing from the framework of at least one embodiment of the current invention.

In respect of at least one embodiment of the inventive adjustment system, there is provision for the marking laser beam to propagate from a laser source that generates it through to a detection plane.

The laser source is preferably embodied as a self-contained laser unit. It is advantageously embodied as a bought-in part, has a controller that is independent of and separate from an imaging modality. In another example the operation of the laser source can however also be controlled by the controller of an imaging modality. The laser source serves to generate laser light as well as to form the beam of one of the beam patterns mentioned above. Especially advantageous is a laser source that is configured to change the beam pattern or the beam form of the marking laser beam, e.g. to adapt it to individual requirements of an examination object, in particular of a patient, or individual requirements of an image measurement.

The detection plane is advantageously embodied so that the entire marking laser beam, which means its entire beam pattern, can be received. The detection plane has one or a previously defined location or distance from the laser source. It is especially advantageous for the central beam of the marking laser beam and surface normals of the detection plane to run in parallel. In this way for example, in the case of a fanned-out beam pattern, the detection surface can advantageously be kept small, which saves space and material costs.

The detection plane comprises a detection unit. This is configured to detect, to recognize or to capture laser light, in particular laser light of the wavelength spectrum emitted by the laser source. In other words the detection unit comprises at least one optical sensor for detection of laser light. The detection unit is also embodied such that it recognizes laser light in the central target position and/or in the at least one peripheral target position. Thus the detection unit is arranged either in the target positions for the central and the at least one peripheral marking laser beam or the detection unit is embodied to recognize laser light position-specifically. In other words the detection unit comprises a detector panel, so that the detection unit, in the second alternative mentioned, not only recognizes whether there is incident laser light, but also where there is incident laser light. The detection unit can be embodied for example as a local photodiode, as a flat photodiode array or as a camera, preferably as a CCD camera.

The detection unit is preferably configured to adapt the target positions for the central beam and the at least one peripheral beam automatically to a changed beam pattern. For example for this purpose the detection unit can also be arranged for adjustment, but also, in the case of a position-sensitive embodiment of the detection unit, can be controllable such that any given positions within a detector panel of the detection unit are defined as target positions. As an alternative the detection unit comprises a plurality of detector elements, which are distributed in the detection plane corresponding to target positions for a central beam and at least one peripheral beam of the marking laser beam for a plurality of beam patterns and are activatable in accordance with a current beam pattern.

The target positions for the central and the at least one peripheral laser beam each have a fixed and in particular invariable location or distance relative to the imaging modality or to reference points of the imaging modality, in particular to its isocenter. This makes it possible to align an examination object, following on from the adjustment method, relative to the imaging modality.

It is assumed below, without restricting the general applicability, that a patient is the examination object, wherein this mostly involves a human being. Basically however the patient can also be an animal. Therefore the two terms "examination object" and "patient" are also used synonymously below. The examination object can however also be a plant or a non-living object, e.g. a historical artifact or the like.

In a preferred version of at least one embodiment of the invention, the laser source is arranged above the entry of an imaging tunnel of an imaging modality, in particular of a computed tomography apparatus or of a magnetic resonance tomography apparatus, and the marking laser beam is aligned perpendicularly downwards. The laser source is fastened to the housing of the imaging modality for example. The detection plane is located below the laser source and below the entry of the imaging tunnel for example, on a pedestal of a mobile patient couch fixed relative to the imaging tunnel for example. If an examination object, located on the patient couch, is now moved into the entry of the imaging tunnel, parts or regions of the examination object will be struck by the marking laser beam. This can be used in such a way as to mark regions of interest of a patient. Alternative arrangements of the components of at least one embodiment of the inventive adjustment system with the same effect are likewise conceivable.

With the adjustment method there is provision in accordance with at least one embodiment of the invention to bring or to adjust the marking laser beam automatically, i.e. without the assistance of the operating personnel, into its adjustment target corresponding to the central target position and the at least one peripheral target position, when the marking laser beam is out of adjustment. Before the adjustment of the marking laser beam a test step can be undertaken in one example embodiment of the invention so as to establish whether the marking laser beam is out of adjustment. In such a step it can be tested whether the central beam is located in the central target position or the at least one peripheral beam is located in the at least one peripheral target position in the detection plane. There is further provision for the marking laser beam to be brought step-by-step into the target position in accordance with a first and a second inventive adjustment of the marking laser beam. This procedure advantageously allows adjustment without human checking.

Instead, the basic idea of at least one embodiment of the present invention, during adjustment of the marking laser beam, is to employ an automatic position control. This significantly simplifies and speeds up the preparation of an image measurement.

For this purpose, at least one embodiment of the inventive adjustment system for carrying out of the first and second adjusting step comprises an adjusting unit. In accordance with at least one embodiment of the invention, this can either act on the laser source and/or on the marking laser beam. In this case the adjusting unit can be embodied so that it changes the beam path of the marking laser beam, in that, on activation, it shifts, tilts, inclines or turns the laser source and/or in that it shifts, tilts, inclines or turns an optical element located in the beam path, such as a mirror for example.

In one example of at least one embodiment of the invention the adjusting unit can be arranged inside or outside the laser source, the same applies to the additional optical element. In other words the adjusting unit can be arranged between the housing of the imaging modality and the laser source and to this extent can bring about a movable suspension or attachment of the laser source on the imaging modality. As an alternative the laser source is rigidly connected to the imaging modality and the adjusting unit is arranged between laser source and detection plane, preferably on the housing of the imaging modality. The arrangement of the adjusting unit close to or even in the laser source has the advantageous effect of bringing about a large or wide deflection, shift or adjustment of the marking laser beam in the detection plane with only a slight manipulation of the adjusting unit.

Each inventive adjustment of at least one embodiment of the marking laser beam can encompass a single or a combination of a number of movements and thus manipulations by the adjusting unit. For example a rotation of the marking laser beam by rotating the laser source around a fixed point can be realized. A translation of the marking laser beam in the detection plane can be realized by a shift or tilt of the laser source or of the optical element via the adjusting unit. The individual or combined movements can be realized via an adjustable support of the laser source or of the optical element. To this end the adjusting unit can also comprise at least one support element, which can be embodied for example as a slide rail for movement, for movement, as a tilt joint for tilting and/or as a rotation support. As explained in detail below, the adjusting unit can comprise at least one adjusting element in the form of an actuator or a servo motor.

At least one embodiment of the inventive adjustment system also comprises a control unit. The control unit exchanges data with the detection unit and the adjusting unit. The control unit can additionally also be configured to control the operation of the laser source, in particular to generate an alternate beam pattern. The control unit can be integrated into the controller of an imaging modality or can be embodied as a separate unit therefrom. The control unit receives signals from the detection unit, which specify whether a part beam of the marking laser beam is striking one of the target positions or not.

The control unit, in at least one embodiment, can comprise a computing unit. This is configured to carry out all computing steps related to at least one embodiment of the inventive method and to generate corresponding control signals, in particular for the adjusting unit. In particular the computing unit is configured, by way of routines held in a memory unit for example and also if necessary inputs from operating personnel, to derive a movement pattern for the marking laser beam and translate it into corresponding control signals for the adjusting unit. For example the computing unit is embodied as an FPGA (acronym for "Field Programmable Gate Array") or comprises an arithmetic logic unit.

In accordance with a first example embodiment of the present invention the adjusting of the marking laser beam comprises a translation and/or a rotation of the marking laser beam in the detection plane.

A translation in this case comprises a movement of the marking laser beam along a straight or curved trajectory in the detection plane, wherein each part beam of the marking laser beam, in particular of the central beam and of the at least one peripheral beam, moves along this trajectory. A rotation comprises a movement of the marking laser beam in which a part beam of the marking laser beam is kept in a fixed location and all other part beams of the marking laser beam move around the position of the fixed-location part beam in an orbit.

In one example embodiment of the invention the rotation occurs around the central beam of the marking laser, every other part beam can however also be the center of a rotation. The control unit is configured in accordance with this embodiment, e.g. as a function of an adjustment routine and/or received signals of the detection unit, to establish adjusting steps predetermined by a current beam pattern for the marking laser beam and to translate these into commands for activation of the adjusting unit.

In accordance with a further advantageous embodiment of the present invention, the marking laser beam is adjusted iteratively at least in one step. That means that, in the first and/or second adjustment of the marking laser beam, said beam will be adjusted a number of times, i.e. repeatedly consecutively, by a fixed distance or by a fixed increment in the same direction of movement or in the same form of movement. The direction or the form of movement can have been selected or determined beforehand by the user or automatically by the control unit, the same applies to the movement increment. This method of operation is based on the basic idea that, even if the current position of the marking laser beam is not known at the beginning of the adjustment method, with repeated execution of one and the same movement step the marking laser beam is bound to strike one of the target positions. Consequently this method of operation dispenses with a prior determination of an initial position or current location of the marking laser beam.

It is possible for the marking laser beam to be out of adjustment, i.e. to have moved away from its adjustment target position such that, with the previously described iterative adjustment of the marking laser beam, the range of adjustment of the adjusting unit is exhausted in the movement direction determined before the marking laser beam has struck one of the target positions for the central beam or the at least one peripheral beam in the detection plane.

In this event, in accordance with another embodiment of the present invention there is provision for an adjustment to be made in another movement direction, provided an adjustment range of the adjusting unit has been exhausted during adjustment of the marking laser beam in a previous movement direction before a target position has been struck by the marking laser beam.

In this way it is insured that the adjustment method is continued and the marking laser beam 'will continue to be looked for' beyond the limit of the adjustment range of the adjusting unit in one direction of movement. In a preferred example embodiment of the invention, the other movement direction can be assumed by reversing the direction of movement.

As an alternative the other movement direction corresponds to a previously defined or randomly selected movement direction. The other movement direction can also be produced by incrementally altering the previous movement direction, for example by turning by a specific angle, e.g. 5°, 30° or 90°. The alteration of the movement direction is preferably done automatically and without the assistance of operating personnel. A movement alteration can be done a number of times consecutively, provided an adjustment in a movement direction does not cause the marking laser beam to strike one of the target positions. There can be provision for ending the alteration in the direction of movement automatically after a specific number of unsuccessful alterations in the direction of movement, e.g. n=5. In this event the intervention of operating personnel is necessary for the adjustment of the marking laser beam. This can be necessary for example when the adjustment of the marking laser beam has moved beyond the adjustment range of the adjusting unit.

In accordance with a preferred embodiment of the present invention, the first adjustment comprises translating the marking laser beam into a first movement direction or rotating it around the current position of its central beam, until the marking laser beam strikes the central target position. The second adjustment comprises rotating the marking laser beam around the position of its central beam produced from the first adjustment and, by translation of the marking laser beam, striking the central target position again, and doing this until such time as the at least one peripheral target position is struck. It should be noted here that by the correction translation in each iteration step, another position of the central beam is produced as a fixed point of the rotation of the following iteration.

This method of operation corresponds to a preferred, iterative approach. The first adjustment serves to match the position of the marking laser beam to the target position of the central beam in the detection plane. The second adjustment serves, while retaining the match between marking laser beam and the target position of the central beam, also to obtain a match with the target position of the at least one peripheral beam.

The translation of the first adjustment is preferably done in a straight-line movement of the marking laser beam in a previously defined movement direction. As an alternative the marking laser beam is rotated around the current position of its central beam. The first adjustment is undertaken until such time as the marking laser beam strikes the central target position in the detection plane, i.e. until any given part beam of the marking laser beam strikes the central target position. Accordingly the effect of the first adjustment is a match in the position of any given part beam of the marking laser beam and the central target position in the sense of a first approach of the position of the marking laser beam to the adjustment target. Subsequently, the second adjustment has the effect, through the rotation of the marking laser beam around its central beam, that any given part beam of the marking laser beam also strikes the at least one peripheral target position in the detection plane. The second adjustment is made such that both the central target position and also the target position for the at least one peripheral beam will be struck by part beams of the marking laser beam. If an approach of the marking laser beam to the peripheral target position by rotation causes the marking laser beam to move away from the central target position, then the second adjustment also comprises a correction movement for the moving away.

In a preferred example embodiment of the invention, the second adjustment comprises a rotation of the marking laser beam around its central beam or the current position of its central beam, until such time as the peripheral target position of a part beam of the marking laser beam is also struck. Since this rotation, under some circumstances, moves the marking laser beam away from the central target position, the second adjustment in this example also comprises a translation, which is aligned such that the marking laser beam will be kept at the central target position.

In another example embodiment of the invention, the second adjustment comprises a rotation of the marking laser beam around the position of the central target position or around the part beam striking the central target position, until such time as the peripheral target position is also struck by a part beam of the marking laser beam.

In accordance with a further embodiment of the present invention, the second adjustment also comprises translating the marking laser until its central beam strikes the central target position. The effect of this is that the central target position is struck by the central beam of the marking laser beam and the at least one peripheral target position is struck by the at least one peripheral beam of the marking laser beam, i.e. the adjustment target position is reached. Preferably there is provision for this purpose for central beam and the at least one peripheral beam to have a different, in particular a higher, intensity than the remaining part beams of the marking laser beam, for the detection unit to be embodied to measure beam intensities at least in the central and the peripheral target position and transfer them to the control unit and for the control unit to be configured to compare the intensity values obtained with stored intensity threshold values. As an alternative, central beam and peripheral beam can have a different wavelength by comparison with remaining part beams.

In accordance with an alternate embodiment of the present invention, the first adjustment comprises a translation of the marking laser beam to at least one complete orbit in the detection plane, a capturing via the detection unit of relative distances between the position of the central beam at the beginning of the orbital movement in relation in each case to the position of the central beam on the orbit when the marking laser beam strikes the central target position in the detection plane, an establishing of relative distances between the positions of the central beam on the orbit when the marking laser beam strikes the central target position in the detection plane, an establishing of a relative distance between the position of the central beam at the beginning of the orbital movement and the central target position in the detection plane, and a translation of the marking laser beam by the established relative distance, so that the central beam of the marking laser beam strikes the central target position. The second adjustment comprises rotating the marking laser beam until the marking laser beam strikes the at least one peripheral target position.

In accordance with this analytical method of operation of an example embodiment, before a correction movement of the marking laser beam, first of all a distance between the central beam or its relative location in relation to the central target position is established. To this end the marking laser beam is adjusted, starting from its current, as a rule unknown, position at the beginning of the adjustment method, to a closed orbit. Depending on the embodiment of the beam pattern and also the initial position of the marking laser beam before the adjustment method, hit positions on the orbit are established, in which the marking laser beam with any given part beam strikes the central target position.

During the orbital movement four, two or no hit positions can be produced. In the event of no hit position, another starting position for the marking laser beam is selected, for example at random, in that this is adjusted in any given way in the detection plane via the adjusting unit. In the event of the presence of two hit positions for an orbital movement, the marking laser beam is likewise adjusted as widely as possible within the adjustment range of the adjusting unit and once again an orbital movement is made, until once again two hit positions have been found per orbital movement.

When four hit positions are found per orbital movement the hit positions opposite one another on the orbit traveled can be connected virtually. The intersection point of the crossing connection lines corresponds to the central target position. In the event of two hit positions for an orbit traveled, the hit positions of an orbit can be connected virtually. The central target position is located where the extended connecting lines cross.

The hit positions each have a relative distance from the starting position of the central beam for the respective orbital movement. After the relative location of the hit positions in relation to the central target position in the detection plane has been established, the relative distance between central target position and the starting position of the central beam can be reconstructed geometrically. The central beam or the marking laser beam will subsequently be adjusted by this relative distance, so that the central beam strikes the central target position. In order to reach the adjustment target, the marking laser beam is subsequently rotated around the central target position, until the at least one peripheral beam also strikes the peripheral target position.

In one embodiment of the present invention, the detection unit of the adjustment system, as already mentioned above, comprises a position-sensitive detector panel.

The detector panel is preferably embodied flat and configured to detect laser light and to encode the position within the detector panel at which there is incident laser light. The detector panel is preferably arranged opposite the laser source and perpendicular to the direction of propagation of the central beam of the marking laser beam. The detector panel can for example involve a photodiode array or a CCD camera. This embodiment of the detection unit allows an especially flexible adaptation or expansion of central and/or peripheral target position to a changed beam pattern for example, since no mechanical adaptations are required.

In another example embodiment of the invention, the detection unit comprises at least two spatially separated detector elements, for example two individual photodiodes, which are arranged in each case in the detection plane at the central and at the at least one peripheral target position. The individual elements can also be arranged movably or adjustably, in order to be able to react to an adaptation of the beam pattern. In this way it can further be provided that the control unit also predetermines a position of the individual detector elements or controls or predetermines the position encoding of a detector panel.

In a further example embodiment of the invention, which likewise renders a mechanical adaptation of the detection unit to a changed beam pattern unnecessary, a plurality of detector elements is included, which are arranged in positions corresponding to central and peripheral target positions for a plurality of beam patterns in the detection plane.

In an especially preferred embodiment of the present invention, the marking laser beam is embodied in the form of a laser cross, as already mentioned at the start.

In other words, the beam pattern here is a cross hair. This corresponds to conventional beam pattern for a positioning laser beam in medical imaging, as is employed in particular in computed tomography or magnetic resonance tomography. Preferably the cross arms are embodied as separate laser lines crossing one another, which are in a fixed arrangement, in particular at a 90° angle to one another. In an especially preferred embodiment the laser lines each have a length of 50 cm to 70 cm, in particular a length of 60 cm. Thus the marking laser beam is embodied essentially to cover the field of view of an imaging modality. The laser lines can be interrupted. In other words the laser lines forming the cross arms will be interrupted so that only an outer area as well as the inner area of the laser lines crossing each other in the center of the marking laser beam can be seen.

Other beam patterns are conceivable in further example embodiments of the invention. In one example the beam pattern can comprise a frame. The frame can be formed by a surrounding laser line, embodied as a straight or curved line. The frame surrounds an illumination-free or at least largely illumination-free inner area. The frame can preferably be embodied round, oval, elliptical or in particular circular in shape. Inside the frame, in particular in the middle of it or in its center, a cross hair can be included, which is formed by two short laser lines crossing one another. The laser line forming the frame in particular has no connection to laser lines of a cross hair or a center point marking. As an alternative, the frame can be embodied square or rectangular. The frame can be closed or interrupted. In the latter case the frame can be formed by individual laser line segments separated from one another or interrupted. There can be provision in example embodiments of the invention for the frame of the beam pattern to comprise additional laser lines, which correspond to extensions of laser lines forming a central cross hair.

In another embodiment of the invention, the adjusting unit of the inventive adjustment system comprises at least one actuator or servo motor. Both embodiment variants, together with at least one support element likewise encompassed by the adjusting unit such as rails, articulated joints and/or bearings, convert electrical control signals into mechanical movement. This can involve a straight-line adjustment, an inclination or tilting, a rotation or combinations thereof, which leads in each case to a change of position and/or an alteration of the alignment or orientation of laser source and/or of an optical element acting on the marking laser beam. Individual forms of movement can be realized by one or more actuators or servo motors.

At least one embodiment of the invention further relates to an imaging modality for auto adjustment of a marking laser beam comprising an inventive adjustment system.

In other words, at least one embodiment of the inventive imaging modality integrates all components of at least one embodiment of the inventive adjustment system into itself. In particular the control unit of the adjustment system can be embedded into the controller of the imaging modality.

The imaging modality can in particular involve a computed tomography apparatus or a magnetic resonance tomography apparatus. Also possible and within the spirit of the invention are embodiments as a C-arm x-ray device or angiography apparatus.

FIG. 1 shows an inventive medical imaging modality in an example embodiment, namely in the form of an x-ray computed tomograph 20. The computed tomograph 20 shown here has a recording unit 24, comprising an x-ray emitter and also an x-ray image detector (not shown). X-ray emitter and x-ray image detector lie inside the recording unit 24 and are covered by the housing of the modality 20. The recording unit 24 rotates during the recording of x-ray projections around a system axis 18. The examination object 16, here a patient 16, lies during the recording of projections on a patient couch 14. The patient couch 14 is designed to move the patient 16 in a direction of recording through the opening 22 or imaging tunnel 22 of the recording unit 24. As a rule the recording direction is given by the system axis 18, around which the recording unit 24 rotates during recording of x-ray projections.

The x-ray computed tomograph 20 comprises an inventive adjustment system. To this end a laser source 8 in the form of a laser 8 for laser beam generation and beam forming is provided. The laser source 8 is arranged above the entry of the opening 22 and is fixed to the housing. It generates a cross-shaped, fanned-out marking laser beam 2 here comprising a central beam 4 in its center and two laser lines crossing in the center, wherein one end of each of the cross arms forms a peripheral beam 6. Other beam patterns or beam forms are likewise possible.

In particular the laser source 8 is configured to adapt a beam form to a desired image measurement. The marking laser beam 2 essentially propagates perpendicularly downwards and strikes a detection plane 10, which is arranged by a flat surface 10 on a fixed-location couch pedestal 12 of the imaging modality 20 and which projects at least partly into the opening 22.

The couch pedestal 12 is used for a soft and secure transport of the patient couch 14 along the system axis 18 before, during and after an image measurement. The couch 14 can be moved far enough on the couch pedestal 12 out of the opening 22 for it to reveal the detection surface 10, for example for an inventive adjustment of the marking laser beam 2.

The detection plane 10 comprises a number, here three, target positions sc, sz and sx for the marking laser beam 2. Sc corresponds to a central target position for the central beam 4 and sx and sz correspond to peripheral target positions for the peripheral beam 6. The target positions sc, sz and sx correspond to an adjustment target.

In accordance with an embodiment of the invention they can be adapted to the beam pattern, in particular the distances and/or locations of the target positions sc, sx and sz can be adapted absolutely and/or relative to one another. In such cases there can be provision for the target positions always to have a defined distance or a defined location in relation to the imaging modality 20, in particular to its isocenter.

As an alternative this distance can also be calibrated in a separate method. The detection plane 10 also comprises a detection unit 11. In the example embodiment shown detector elements 13 in the form of intensity-sensitive photodiodes 13 are arranged, in the target positions sc, sx and sz in, on or under the detection plane 10. These are configured to detect whether there is incident laser light in at least one of the target positions sc, sx or sz. The detector elements 13 can also establish the intensity of incident laser light.

Figure 2:
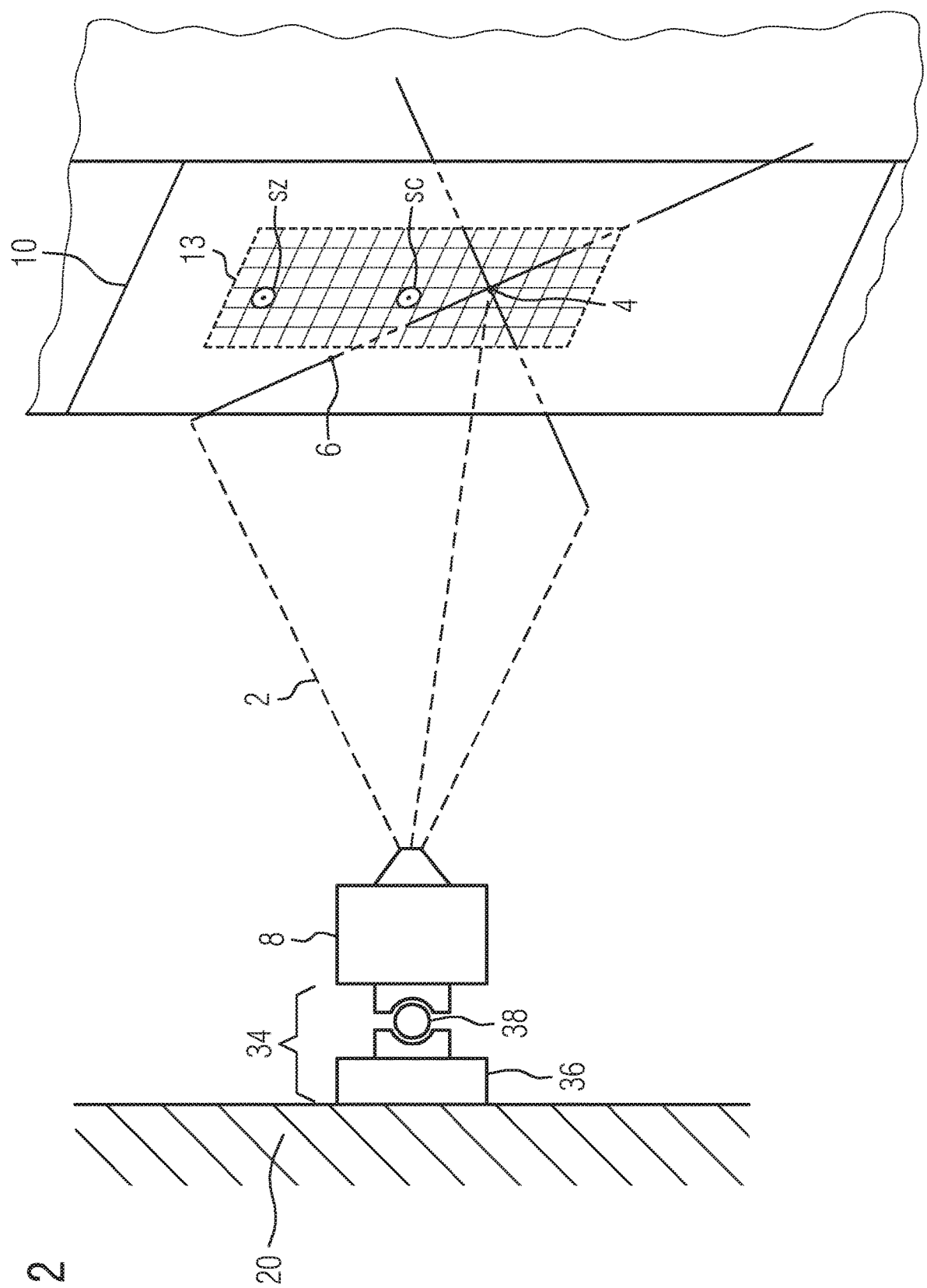
FIG. 2 shows a schematic diagram of an inventive adjustment system in an example embodiment.

In alternate versions of the imaging modality the detection unit 11 comprises at least one flat detector panel 13 as detector element 13, for example in the form of a photodiode array or a CCD camera, which is configured to detect incident position and intensity of incident laser light. An example of this is shown in FIG. 2.

The at least one detector panel 13 can essentially cover the detection plane 10 but can also be arranged in preferred areas of the detection plane 10, in which at least one of the target positions sc, sx or sz is arranged. The detector panel 13 comprises a plurality of pixel rows and pixel columns, wherein a target position comprises at least one or a group of adjacent pixels in each case.

Not shown in FIG. 1, but likewise encompassed by an embodiment of the inventive imaging modality 20, is an adjusting unit 34 for adjustment of the marking laser beam 2 in the detection plane 10. The adjusting unit 34 will be described in greater detail with reference to FIG. 2. At least adjusting unit 34 and detection unit 11 are in data communication with a control unit 26 likewise encompassed by the imaging modality 20.

The data connections in each case, in the known manner, are realized as wired or wireless connections. The detection unit 11 is configured to transfer signals to the control unit 26, which specify for example whether the marking laser beam 2 is striking one of the target positions sc, sx or sz and in particular also, what the incident light intensity is in at least one of the target positions sc, sx or sz.

The control unit 26 can be embodied as a self-contained control unit or as part of a control unit of the imaging modality 20. The control unit 26 is also in data communication with an input/output unit 32. The input/output unit 32 serves for example to display graphically the selection options for a desired adjustment routine or to display possible intensity threshold values for the laser light to a user. The input/output unit 32 can involve an LCD, plasma or OLED screen for example. It can furthermore involve a touch-sensitive screen.

The input/output unit 32 also involves a keyboard, a mouse, a so-called touch screen or also a microphone for voice input for example. The input/output unit 32 can also be configured to recognize movements of a user and translate them into corresponding commands.

The control unit 26 is configured to process signals received from the detection unit 11 and/or the input/output unit 32 for example and, within the framework of the inventive adjustment method, to create control signals, in particular control signals for the adjusting unit 34. For this purpose the control unit 26 comprises a computing unit 28, which on the one hand is configured, in accordance with an adjustment routine or an adjusting step sequence chosen by a user for example and/or a current beam pattern of the marking laser beam 2, to establish adjusting steps for the marking laser beam 2 and to create corresponding control signals for the adjusting unit 34.

Various adjustment routines, which in particular are adapted or optimized to a specific beam pattern, can be held in a memory 30 likewise encompassed by the control unit 26. In this context the computing unit 28 is also configured, on the basis of the signals captured by the detection unit 11, to establish in relation to the target positions sc, sx or sz whether the marking laser beam 2 is striking at least one of the target positions or whether the central beam 4 and/or the at least one peripheral beam 5 is striking one of the target positions.

The computing unit 28 can interoperate with a computer-readable data medium, in particular in order to carry out an inventive method by a computer program with program code. Furthermore the computer program can be stored for retrieval from the machine-readable medium. In particular the machine-readable medium can involve a CD, DVD, Blu-Ray disk, a memory stick or a hard disk. The computing unit 28 can be embodied in the form of hardware or in the form of software. For example the computing unit 28 is embodied as an FPGA (acronym for "Field Programmable Gate Array") or comprises an arithmetic logic unit.

In the example shown here at least one computer program is stored in the memory 30 of the control unit 26, which carries out all method steps of embodiments of the inventive method when the computer program is executed. The computer program for execution of the method steps of embodiments of the inventive method comprises program code. Furthermore the computer program can be embodied as an executable file and/or be on another computer system. For example the medical imaging modality 20 can be designed so that the computing unit 28 loads the computer program for executing embodiments of the inventive method into its internal working memory via an intranet or via the Internet.

All the units can be physically or functionally connected to one another.

FIG. 2 shows an embodiment of an inventive adjustment system in an example embodiment. It comprises a laser 8, which emits a marking laser beam 2 in the direction of the detection plane 10, here in the form of a cross hair with interrupted laser lines crossing one another. The central beam 4 of the marking laser beam 2 is formed at the crossing point of the laser lines forming the beam. A cross arm comprises at its outer end a peripheral beam 6.

In this example embodiment the central beam 4 of the marking laser beam 2 essentially runs perpendicularly, any other beam courses are likewise possible. The laser 8 is arranged on the outer wall or the housing of an imaging modality 20, an adjusting unit 34 comprising an adjusting element 36 in the form of at least one servo motor 36 and/or an actuator 36 as well as at least one adjustable support element 38, which transmits a movement of the adjusting element 36 to the laser 8, functions as a linking element.

In the present case the support element 38 is embodied as a ball joint 38 able to be tilted and especially rotated in all directions. This embodiment of the support element 38 makes possible both any given translation of the marking laser beam 2 by tilting the laser 8 in the detection plane 10 and also a rotation of the marking laser beam 2 around its central beam 4.

Also conceivable are alternate embodiments of the adjusting unit 34. For example a number of support elements 38 in the form of adjustment rails 38, each for a different movement direction, a number of tilt joints 38, each for a different movement direction and/or rotary bearing for rotation movements can be provided. Accordingly the adjusting element 36 can comprise one or more actuators or servos, wherein each of them, together with a corresponding support element 38, can be responsible for one or more directions of movement.

As an alternative, adjusting units 34 additionally comprise an optical element, for example in the form of at least one mirror, which is arranged in the beam path of the marking laser beam 2 and on which an adjusting element 36 acts via a corresponding support element 38. In these alternate embodiments the laser 8 is attached immovably as a rule, so that the adjustment merely comprises a manipulation of the course of the marking laser beam 2, but not of the laser 8. The alternate adjusting unit 34 can be arranged in the laser source 8 or outside the laser source, then preferably also on the housing of the imaging modality 20.

In the present example embodiment, the detection plane 10 comprises two target positions sc and sx. Sc represents the target position for the central beam 4 and sx the target position for the peripheral beam 6, wherein the two target positions sc and sx together correspond to the adjustment target of an embodiment of an inventive adjustment method. Here the marking laser beam 2 does not strike either the central or the peripheral target position sc, sx in the detection plane 10.

In other words the marking laser beam 2 is out of adjustment. The deviations in position and angle typically correspond to a few millimeters or a few degrees. These deviations are regularly produced by mechanical work on the imaging modality 20, in which for example housing parts comprising the laser 8 must be removed. However vibrations during operation of the imaging modality 20 can also cause misalignment of the marking laser beam 2 over time. Deviations to the degree mentioned above are able to be corrected in a simple, fast and exact manner by the inventive adjustment method, as is described in detail below with reference to FIGS. 3 to 7. Only in the cases in which the deviations are greater than the typical values specified will the intervention of or a correction by the user be required according to embodiments of the invention.

Figure 4:
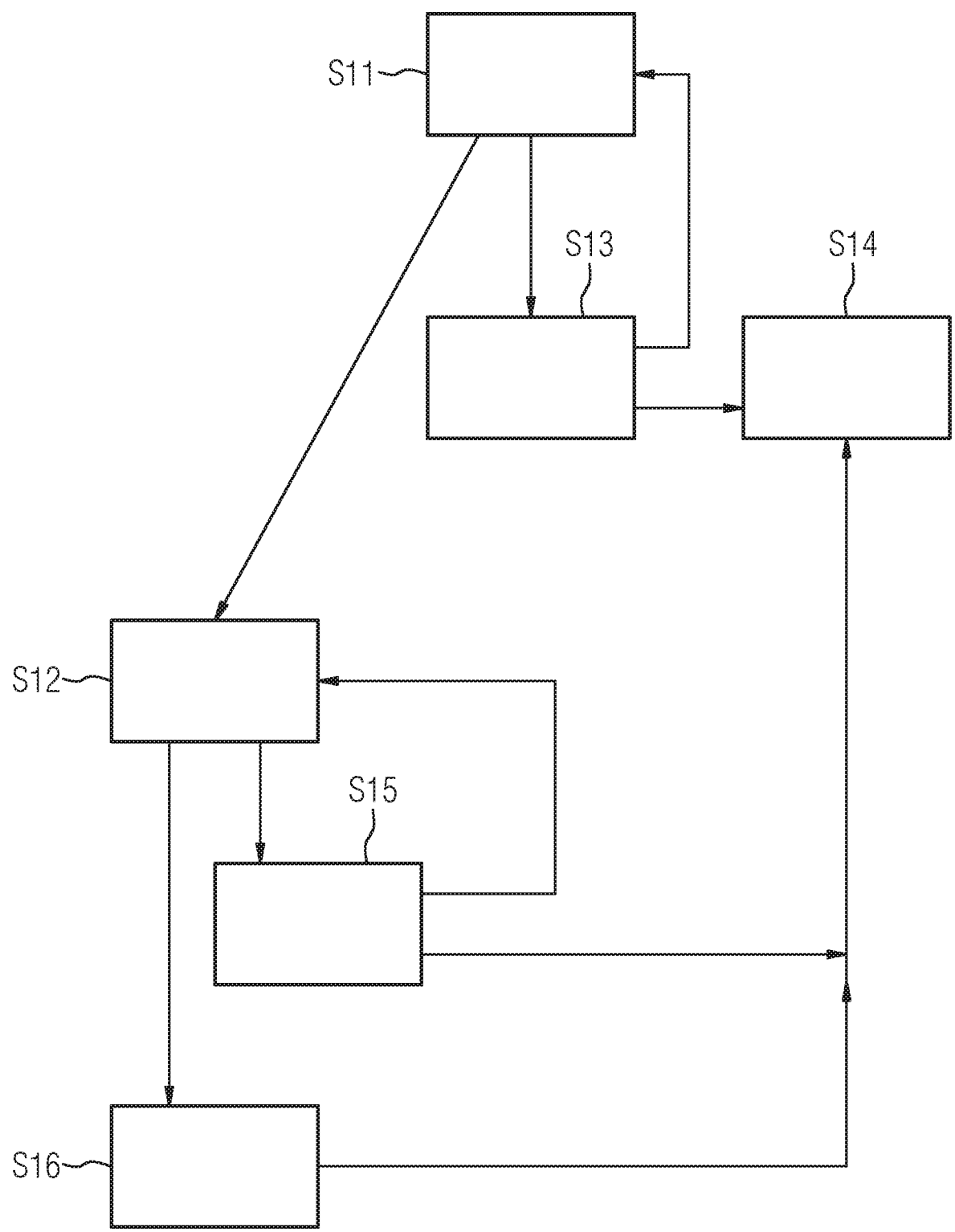
FIG. 4 shows a block schematic of an inventive adjustment method in an example embodiment.

FIG. 4 shows a first example embodiment of an inventive, here iterative, adjustment method as a block schematic. In this example embodiment a current position of the out-of-adjustment marking laser beam 2 is not known and will also not be established. Instead this embodiment variant makes provision for a step-by-step approach of the position of the marking laser beam 2 to the adjustment target in the sense of a trial-and-error method.

Figure 3:
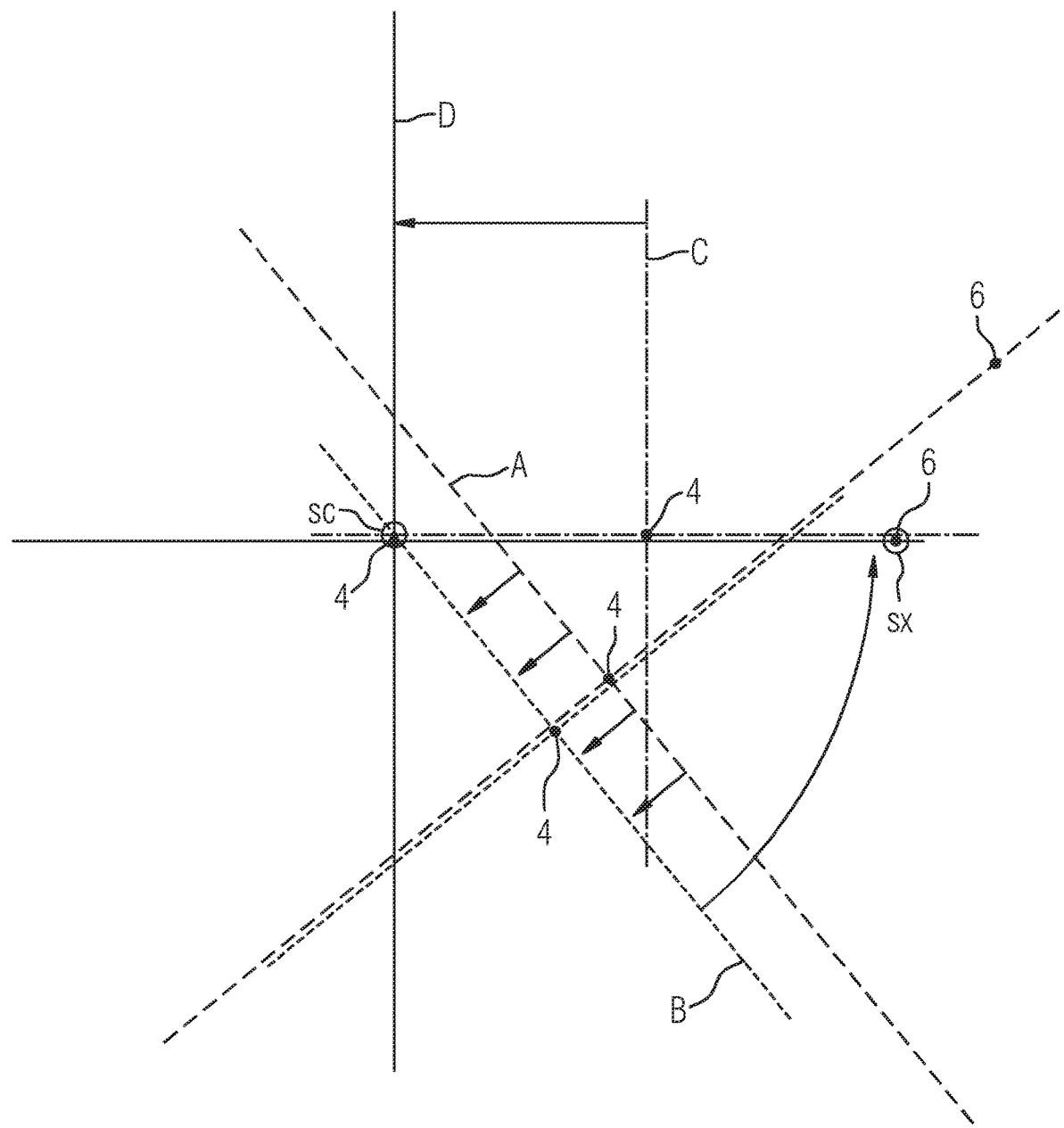
FIG. 3 shows a schematic diagram of an inventive adjustment system in another example embodiment.

Starting point of this process is a marking laser beam 2 (long dashed lines), which is arranged in accordance with the position A shown in FIG. 3 and deviating from the target positions sc and sx. In accordance with an embodiment of the invention there is provision for moving the marking laser beam 2 in a step S11 via adjusting unit 34 in a random previously defined direction (shown in FIG. 3 by the straight arrows), until any given part beam of marking laser beam 2 strikes the central target position sc. As an alternative step S11 can also comprise rotating the marking laser beam 2 around its central beam 4 in a direction of rotation.

If the adjustment range of the adjusting unit 34 in the selected direction is exhausted, in other words, if the adjustment maximum of this movement direction is reached, before the central target position sc has been struck, the marking laser beam 2 will be moved back into its starting position corresponding to position A. In a step S13 another movement direction is selected by the control unit 2 at random or in accordance with a stored scheme 6 and the marking laser beam 2 is adjusted according to step S11 to look for a hit on the central target position sc in this direction. Preferably a change of direction is first carried out. This iteration loop is run until such time as either the marking laser beam 2 strikes the central target position sc or all possible directions of movement corresponding to the adjusting unit 34 are exhausted.

For the latter case the adjustment method in accordance with step S14 provides for a warning signal to be output to a user, which signals that a manual adjustment or even a repair is necessary. This warning signal can be output optically for example via the input/output unit 32 or acoustically. If the detection unit 11 detects for example via a sudden increase in intensity at the detector element 13 arranged in the central target position sc during the adjustment in accordance with step S11, a hit of the marking laser beam 2, the marking laser beam 2 (short dashed line) has assumed the position B shown in FIG. 3.

In a step S12 the control unit 26 now controls the adjusting unit 34 such that the marking laser beam 2 rotates around a central beam 4 and at the same time is moved into the central target position sc again, until a given part beam of the marking laser beam 2 also strikes the peripheral target position sx. The rotation is done incrementally preferably only by slight degree values of for example 0.2° or 0.5°, so that advantageously only small correction movements are needed to bring the marking laser beam 2 into the central target position sc again. If the adjustment range of the adjusting unit 34 in the selected direction of rotation is exhausted, before the peripheral target position sx has been struck, the marking laser beam 2 will be moved back into the position B.

In a step S15 another movement direction, here in particular the opposing direction of rotation and an opposing correction direction for maintaining the central target position sc are selected by the control unit 26 and the marking laser beam 2 is adjusted in accordance with step S12 to look for a hit on the peripheral target position sx. For unsuccessful, that is to say hitless, exhaustion of the adjustment range, even in this direction, a warning signal in accordance with step S14 is again output. If the effect of the rotation around the central beam 4 is an overlaying of marking laser beam 2 and peripheral target position sx, the marking laser beam 2 (dotted and dashed line) is assumed for example to have reached the position C shown in FIG. 3.

In a step S16 the adjusting unit 34 is now instructed by the control unit 26 to effect a movement of the marking laser beam 2 in a direction corresponding to the virtual connection line of the central and the peripheral target positions sc, sx, until such time as the central beam 4 strikes the central target position sc and/or the peripheral beam 6 strikes the peripheral target position sx. To this end there can be provision for the marking laser beam 2, in its central beam 4 and its peripheral beam 6, to have an intensity deviating from the remaining part beams, in particular a higher intensity. In each movement step the current intensity values detected in the target positions are transferred to the control unit 26, which in each case carries out a threshold value comparison with intensity values. The threshold value can be defined in advance for example, have been retrieved in advance from the memory 30 or be produced from the (average) intensity values of remaining part beams of the marking laser beam 2, which have already struck the target positions. If the result of the threshold value comparison is a deviation between captured intensity and threshold value, central beam 4 and/or peripheral beam 6 have assumed the respective target position. The marking laser beam 2 (solid line) is now located in the position D shown in FIG. 3 corresponding to the adjustment target. The method is ended.

Figure 7:
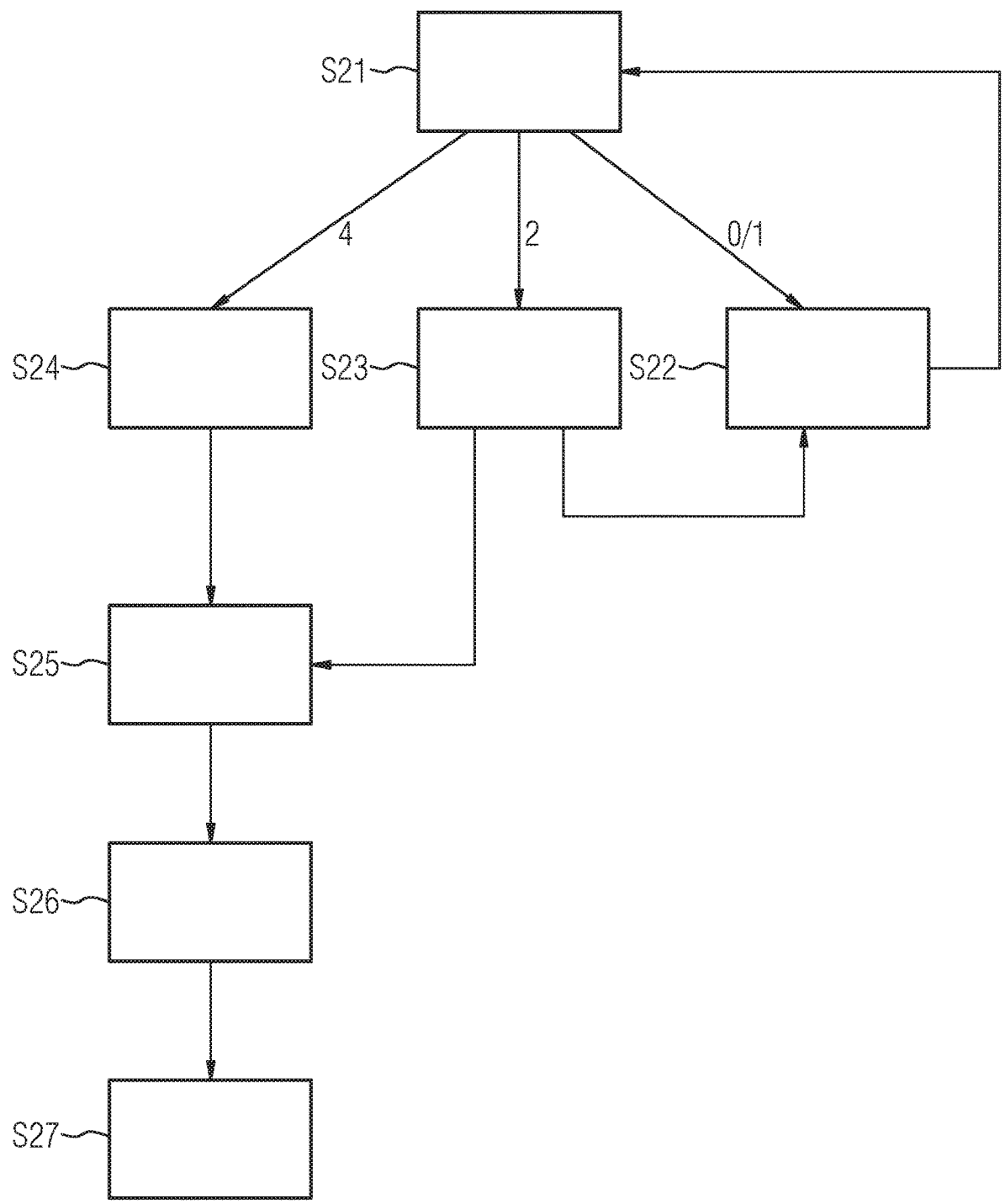
FIG. 7 shows a block schematic of an inventive adjustment method in another example embodiment.

FIG. 7 shows an alternate, partly analytical adjustment method in an example embodiment as a block schematic. Here, before an adjustment of the marking laser beam 2 by the control unit 26, it is established where the central beam 4 of the marking laser beam is located relative to the central target position sc and it is only subsequently moved by this relative distance.

Figure 5:
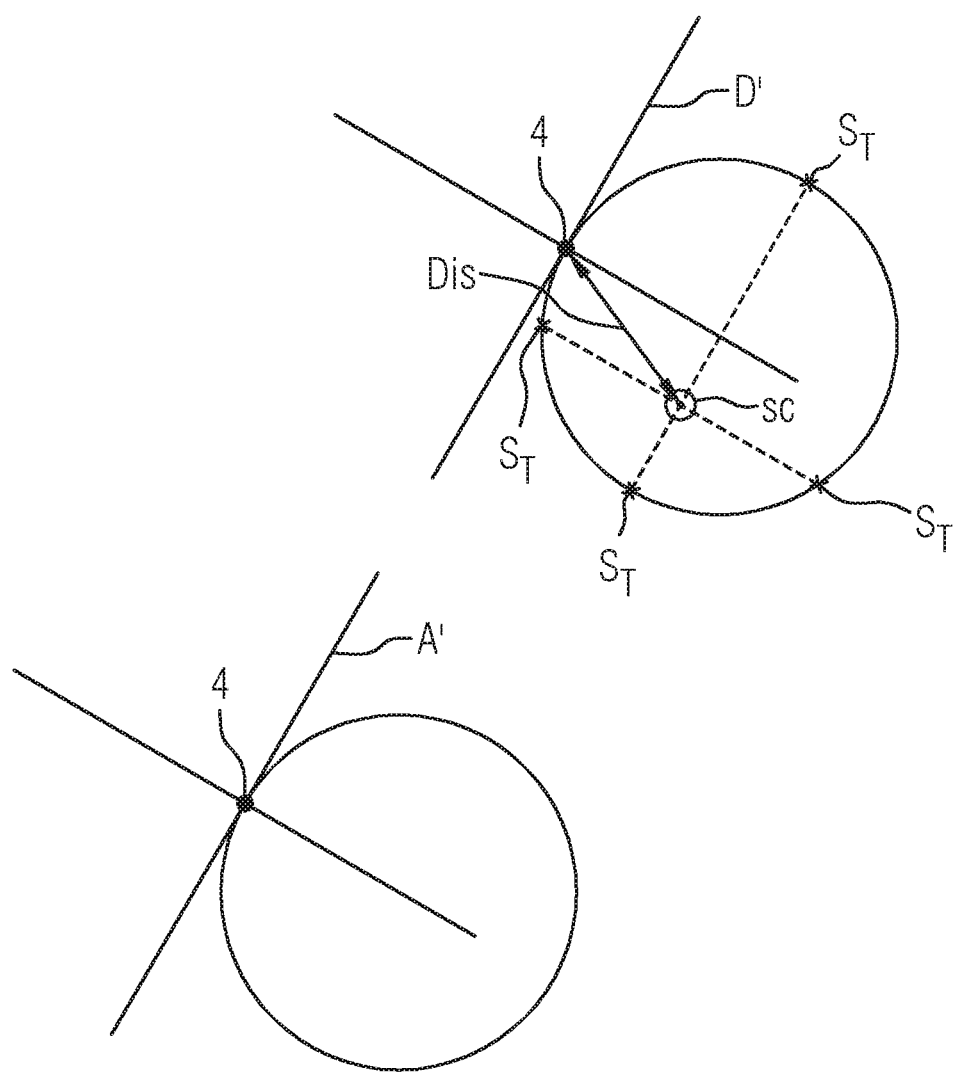
FIG. 5 shows a schematic diagram of an inventive adjustment system in a further example embodiment.
Figure 6:
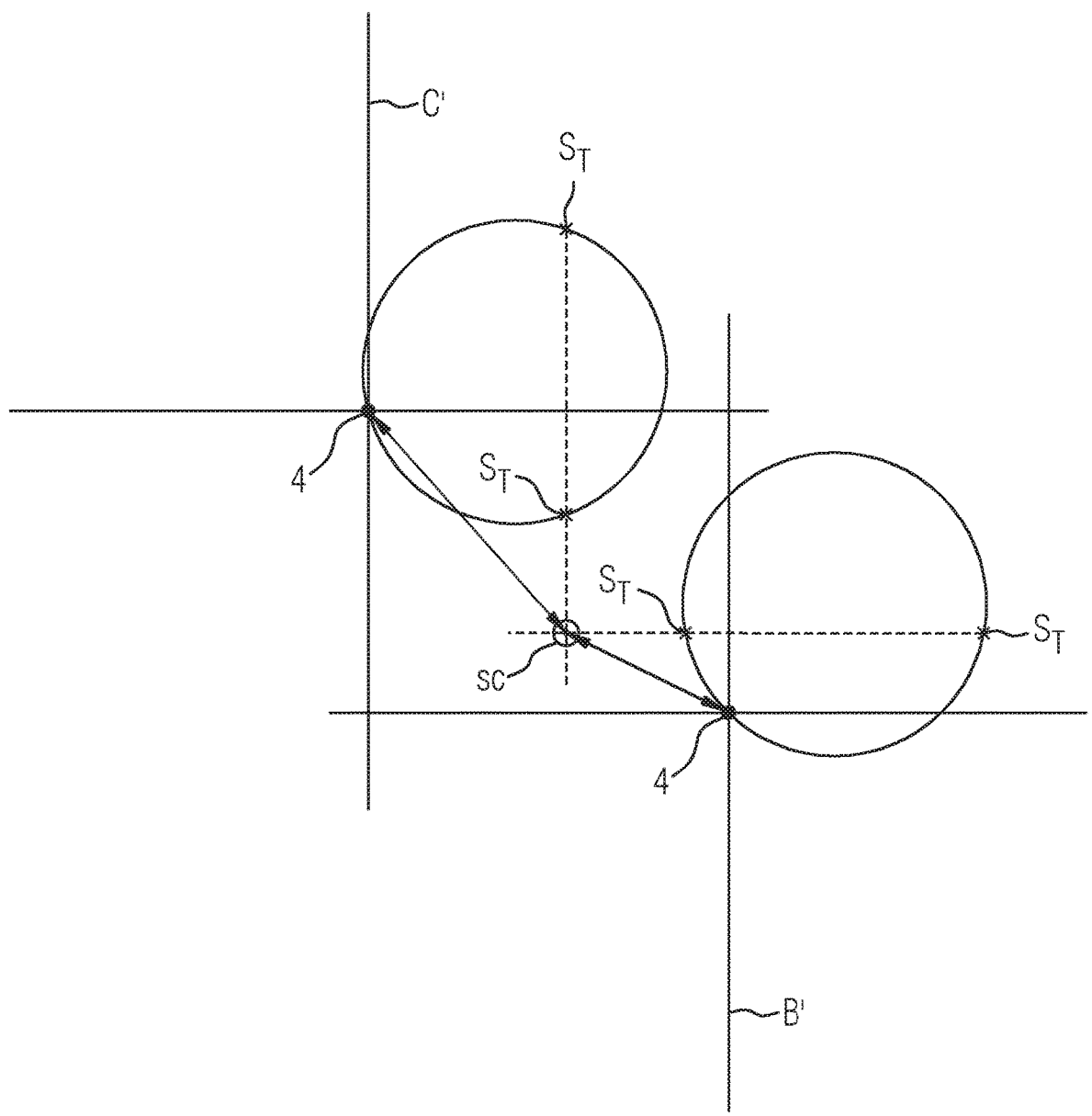
FIG. 6 shows a schematic diagram of an inventive adjustment system in a further example embodiment.

The starting point of this method is again a cross-shaped marking laser beam 2, which is located in a position A', B' or D', shown in FIG. 5 or FIG. 6. In these positions the central beam 4 in each case has an unknown relative distance to the central target position sc in the detection plane 10.

In a first step S21 the marking laser beam 2 is moved by the adjusting unit 34, starting from the position of the central beam 4, on a closed orbit in any given direction. The maximum extent of the circle, on the circumferential line of which the orbit runs, is limited by the adjustment range of the adjusting unit. At a minimum the circle should be large enough for it to correspond to a desired adjustment accuracy. For example the circle has a diameter of a few centimeters, in particular 1 cm to 2 cm. The location of the orbit traveled relative to the central target position sc as well as the starting position of the central beam 4, determines whether and how often any given part beam of the marking laser beam 2 strikes the central target position sc, detected in each case by an increase in intensity established by the detection unit 11.

If the orbit originally chosen initially does not produce any hits or produces just one hit, in a step S22 the marking laser beam 2 is moved by the adjusting unit 34 in accordance with the specification of the control unit 26 into another position as far as possible from the original position. The adjustment into the new position can comprise a rotation and/or a shift of the marking laser beam. The movement can be chosen by the control unit 26 at random or corresponding to a predetermined series of steps of a stored adjustment routine.

The new position can be the position B' shown in FIG. 6 for example. There, corresponding to step S21 in the search for hits of marking laser beam 2 and central target position sc an orbit is again traveled, starting from the position of the central beam 4. If 2 hits are produced by this (small crosses on the orbit in FIG. 6), these two relative positions 'starting position of central beam 2—position of central beam 2 at hit' will be buffered by the control unit 26 in accordance with step S23. The marking laser beam 2 is then moved once again into another position, corresponding to position C' for example, shown in FIG. 6, in accordance with step S22, in order, in accordance with step S21, to describe an orbit once again. If two hits are again produced, here too the relative positions will be stored by the control unit 26.

This method of operation is repeated until such time as a total of four hit positions have been detected. If the result of a possible multiply repeated change of the starting position of the marking laser beam 2 for the orbital movement is no hits, after a four-fold or five-fold repetition, the method can be aborted and a warning signal output to the user (cf. also remarks in this connection for FIG. 3). If on the other hand the original starting position of the marking laser beam 2 is the position D' shown in FIG. 5, four hit positions are immediately produced during the first circular movement (small crosses on the orbit in FIG. 5). These will be buffered in step S24 by the control unit 26. In this case no iteration loop needs to be run.

In a step S25 following on from step S23 or step S24 the control unit 26 establishes a relative distance of each of the established hit positions to the central target position sc. To this end the intersection point of connecting lines is established, which a) for four hit positions on an orbit, is produced as the intersection point of the connecting lines (dashed lines in FIG. 5) between hit positions opposite one another on the orbit, or b) for two orbits, each with two hit positions, is produced as the intersection point of the elongated connecting lines (dashed lines in FIG. 6) between the hit positions located in each case on an orbit.

Furthermore, in step S25 this results in the establishment of the relative distance between central target position sc and position of the central beam before orbital movement in one of the positions B', C' or D'. In step S26 the control unit 26 establishes, corresponding to this relative distance, adjustment commands needed for the adjusting unit and the marking laser beam 2 is moved in such a way that its central beam 4 strikes the central target position sc. In a further step S27, the marking laser beam 2 will subsequently be rotated incrementally around the central beam 4 until such time as a peripheral beam 6 strikes a peripheral target position sx, sz. Then the method is ended.

Where this has not yet occurred explicitly, but is sensible and in the spirit of the invention however, individual example embodiments, individual sub aspects or features thereof can be combined with or exchanged with one another, without departing from the framework of the present invention. Advantages of the invention described with regard to one example embodiment also apply, without specific reference thereto, where transferable, to other example embodiments.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An adjustment method for a marking laser beam of an imaging modality, the marking laser beam including a central beam at a relatively center of the marking laser beam and at least one peripheral beam in a relatively outer area of the marking laser beam, and the marking laser beam extending from a laser source configured to generate the marking laser beam to a detection plane, the detection plane including a central target position for the central beam and at least one peripheral target position for the at least one peripheral beam and a detection unit, the detection unit being embodied to capture whether the marking laser beam is striking at least one of the central and at least one target position, the method comprising:
   adjusting the marking laser beam, via an adjusting unit, until the marking laser beam strikes the central target position; and
   adjusting the marking laser beam again, via the adjusting unit, until the marking laser beam strikes the at least one peripheral target position, wherein the marking laser beam is also kept at the central target position.

2. The adjustment method of claim 1, wherein at least one of the adjusting of the marking laser beam and the adjusting the marking laser beam again includes at least one of a translation and a rotation of the marking laser beam in the detection plane.

3. The adjustment method of claim 1, wherein at least one of the adjusting of the marking laser beam and the adjusting the marking laser beam again includes iterative adjusting.

4. The adjustment method of claim 1, further comprising:
   adjusting of the marking laser beam in another movement direction, an adjustment range of the adjusting unit being exhausted during the adjusting of the marking laser beam in a previous movement direction, before the central target position is struck by the marking laser beam.

5. The adjustment method of claim 1, wherein
   the adjusting of the marking laser beam includes translating the marking laser beam into a first movement direction or rotating the marking laser beam around a position of a central beam of the marking laser beam, until the marking laser beam strikes the central target position; and
   the adjusting of the marking laser beam again includes rotating the marking laser beam around the position of the central beam of the marking laser beam produced by the adjusting and by translation of the marking laser beam striking the central target position again, until the at least one peripheral target position is also struck by the marking laser beam.

6. The adjustment method of claim 5, wherein the adjusting of the marking laser beam again further includes translating the marking laser beam, until the central beam of the marking laser beam strikes the central target position.

7. The adjustment method of claim 1, wherein the adjusting of the marking laser beam comprises:
   translating the marking laser beam to at least one complete orbit in the detection plane,
   capturing, via the detection unit, relative distances between a position of the central beam at a beginning of an orbital movement to a respective position of the central beam on an orbit when the marking laser beam strikes the central target position in the detection plane, establishing relative distances between respective positions of the central beam on the orbit when the marking laser beam strikes the central target position in the detection plane, establishing a relative distance between the position of the central beam at the beginning of the orbital movement and the central target position in the detection plane, and translating the marking laser beam by the relative distance established, so that the central beam of the marking laser beam strikes the central target position, and wherein the adjusting of the marking laser beam again comprises rotating the marking laser beam until the marking laser beam strikes the at least one peripheral target position.

8. An adjustment system for a marking laser beam of an imaging modality, comprising a laser source, to generate the marking laser beam, the marking laser beam being configured to propagate from the laser source to a detection plane, and the marking laser beam including a central beam in a center of the marking laser beam and at least one peripheral beam in an outer area of the marking laser beam, a detection unit, arranged in the detection plane, wherein the detection plane includes a central target position for the central beam and at least one peripheral target position for the at least one peripheral beam and wherein the detection unit is configured to capture the marking laser beam striking at least one of the central target position and the at least one peripheral target position, an adjusting unit, configured to adjust the marking laser beam, and a control unit, configured together with detection unit and adjusting unit, to carry out at least adjusting the marking laser beam, via an adjusting unit, until the marking laser beam strikes the central target position, and adjusting the marking laser beam again, via the adjusting unit, until the marking laser beam strikes the at least one peripheral target position, wherein the marking laser beam is also kept at the central target position.

9. An adjustment system for a marking laser beam of an imaging modality, comprising:

a laser source to generate the marking laser beam, the marking laser beam being configured to propagate from the laser source to a detection plane, and the marking laser beam including a central beam in a center of the marking laser beam and at least one peripheral beam in an outer area of the marking laser beam, a detection unit, arranged in the detection plane, the detection plane including a central target position for the central beam and at least one peripheral target position for the at least one peripheral beam, and wherein the detection unit is configured to capture at least one of the central target position and the at least one peripheral target position, an adjusting unit, configured to adjust the marking laser beam, and a control unit, configured, together with detection unit and adjusting unit, to carry out at least:

adjusting the marking laser beam until the marking laser beam strikes the central target position, and adjusting the marking laser beam again until the marking laser beam strikes the at least one peripheral target position, wherein the marking laser beam is also kept at the central target position.

10. The adjustment system of claim 8, wherein the detection unit includes a position-sensitive detector panel.

11. The adjustment system of claim 8, wherein the marking laser beam is embodied in a form of a laser cross.

12. The adjustment system of claim 8, wherein the adjusting unit includes at least one actuator or servo motor.

13. The adjustment system of claim 8, wherein laser source, adjusting unit and detection unit are arranged on a housing of the imaging modality.

14. An imaging modality for auto-adjustment of a marking laser beam comprising:

the adjustment system of claim 8.

15. The adjustment method of claim 2, wherein at least one of the adjusting of the marking laser beam and the adjusting the marking laser beam again includes iterative adjusting.

16. The adjustment method of claim 2, further comprising:

adjusting of the marking laser beam in another movement direction, an adjustment range of the adjusting unit being exhausted during the adjusting of the marking laser beam in a previous movement direction, before the central target position is struck by the marking laser beam.

17. The adjustment method of claim 3, further comprising:

adjusting of the marking laser beam in another movement direction, an adjustment range of the adjusting unit being exhausted during the adjusting of the marking laser beam in a previous movement direction, before the central target position is struck by the marking laser beam.

18. The adjustment method of claim 2, wherein the adjusting of the marking laser beam includes translating the marking laser beam into a first movement direction or rotating the marking laser beam around a position of a central beam of the marking laser beam, until the marking laser beam strikes the central target position; and the adjusting of the marking laser beam again includes rotating the marking laser beam around the position of the central beam of the marking laser beam produced by the adjusting and by translation of the marking laser beam striking the central target position again, until the at least one peripheral target position is also struck by the marking laser beam.

19. The adjustment method of claim 18, wherein the adjusting of the marking laser beam again further includes translating the marking laser beam, until the central beam of the marking laser beam strikes the central target position.

20. The adjustment system of claim 9, wherein the detection unit includes a position-sensitive detector panel.

21. The adjustment system of claim 9, wherein the marking laser beam is embodied in a form of a laser cross.

22. The adjustment system of claim 9, wherein the adjusting unit includes at least one actuator or servo motor.

23. The adjustment system of claim 9, wherein laser source, adjusting unit and detection unit are arranged on a housing of the imaging modality.

* * * * *